US007015360B2

(12) United States Patent
Whiteker et al.

(10) Patent No.: US 7,015,360 B2
(45) Date of Patent: Mar. 21, 2006

(54) ASYMMETRIC CATALYSTS PREPARED FROM OPTICALLY ACTIVE BISPHOSPHITES BRIDGED BY ACHIRAL DIOLS

(75) Inventors: Gregory Todd Whiteker, Charleston, WV (US); Jerzy Klosin, Midland, MI (US); Kelli Jo Gardner, Winfield, WV (US)

(73) Assignee: Dow Global Technologies, Inc., Midland, MI (US)

( * ) Notice: Subject to any disclaimer, the term of this patent is extended or adjusted under 35 U.S.C. 154(b) by 346 days.

(21) Appl. No.: 10/401,464

(22) Filed: Mar. 28, 2003

(65) Prior Publication Data

US 2004/0199023 A1    Oct. 7, 2004

(51) Int. Cl.
*C07C 45/50* (2006.01)
*C07F 9/02* (2006.01)
*B01J 31/00* (2006.01)
*B01J 27/185* (2006.01)

(52) U.S. Cl. ..................... 568/429; 568/454; 568/568; 568/15; 502/155; 502/213

(58) Field of Classification Search ................ 568/429, 568/454, 15; 502/155, 213
See application file for complete search history.

(56) References Cited

U.S. PATENT DOCUMENTS 4,268,688 A * 5/1981 Tinker et al. ................ 560/177
5,491,266 A * 2/1996 Babin et al. ................ 568/449

OTHER PUBLICATIONS

Buisman et al. Chiral Cooperativity in Diastereomeric Diphosphite Ligands: Effects on the Rhodium-Catalyzed Enantioselective Hydroformylation of Styrene. Organometallics. 1997, vol. 16, p 2929-2939.*

* cited by examiner

*Primary Examiner*—Sikarl A. Witherspoon

(57) ABSTRACT

This invention relates to asymmetric hydroformylation (hf) processes in which a prochiral or chiral compound is contacted in the presence of an optically active metal-ligand complex catalyst to produce an optically active aldehyde or product derived from an optically active aldehyde. The invention encompasses novel ligands and catalysts for use in such processes.

44 Claims, No Drawings

ASYMMETRIC CATALYSTS PREPARED FROM OPTICALLY ACTIVE BISPHOSPHITES BRIDGED BY ACHIRAL DIOLS

BRIEF SUMMARY OF THE INVENTION

1. Technical Field

This invention relates to asymmetric hydroformylation (hf) processes in which a prochiral or chiral compound is contacted in the presence of an optically active metal-ligand complex catalyst to produce an optically active aldehyde or product derived from an optically active aldehyde. The invention encompasses novel ligands and catalysts for use in such processes.

2. Background of the Invention

Asymmetric synthesis is of importance, for example, in the pharmaceutical industry, since frequently only one optically active isomer (enantiomer) is therapeutically active. An example of such a pharmaceutical product is the non-steroidal anti-inflammatory drug Naproxen. The S enantiomer is a potent anti-arthritic agent while the R enantiomer is a liver toxin. It is therefore often desirable to selectively produce one particular enantiomer over its mirror image.

It is known that special precautions must be taken to ensure production of a desired enantiomer because of the tendency to produce optically inactive racemic mixtures, that is equal amounts of each mirror image enantiomer whose opposite optical activities cancel out each other. In order to obtain the desired enantiomer or mirror image stereoisomer from such a racemic mixture, the racemic mixture must be separated into its optically active components. This separation, known as optical resolution, may be carried out by actual physical sorting, direct crystallization of the racemic mixture, or other methods known in the art. Such optical resolution procedures are often laborious and expensive as well as destructive to the desired enantiomer. Due to these difficulties, increased attention has been placed upon asymmetric synthesis in which one of the enantiomers is obtained in significantly greater amounts.

Asymmetric hydroformylation of olefins is especially valuable for the synthesis of optically active products, since the reaction is a one-carbon homologation that also establishes a chiral center. Efficient asymmetric hydroformnylation desirably affords the ability to control both regioselectivity (branched/linear ratio) and enantioselectivity. The optically active aldehyde that is produced in asymmetric hf can be further elaborated into other functional groups, either by subsequent reaction steps or via in situ reaction with other reagents.

Various asymmetric hydroformylation catalysts have been described in the art, see van Leeuwen, P. W. N. M. and Claver, C., "Rhodium Catalyzed Hf", Kluwer Academic Publishers, Dordrecht, 2000. For example, Stille, John K. et al., Organometallics 1991, 10, 1183–1189 relates to the synthesis of three complexes of platinum(II) containing the chiral ligands 1-(tert-butoxycarbonyl)-(2S, 4S)-2-[(diphenylphosphino)methyl]-4-(dibenzophospholyl)pyrrolidine, 1-(tert-butoxycarbonyl)-(2S,4S)-2-[(dibenzophospholyl)methyl]-4-(diphenylphosphino)pyrrolidine and 1-(tert-butoxycarbonyl)-(2S,4S)-4-(dibenzophospholyl)-2-[(dibenzophospholyl)methyl]pyrrolidine. Asymmetric hydroformylation of styrene was examined with use of platinum complexes of these three ligands in the presence of stannous chloride as catalyst. Various branched/normal ratios (0.5–3.2) and enantiomeric excess values (12–77%) were obtained. When the reactions were carried out in the presence of triethyl orthoformate, all four catalysts gave virtually complete enantioselectivity (ee>96%) and similar branched/normal ratios. However, platinum hydroformylation catalysts are of limited utility due to their low catalytic activity and requirement for high CO—$H_2$, i.e. syn gas, pressures.

Phosphite ligands are especially effective for use in asymmetric hydroformylation processes. For example, Wink, Donald J. et al., Inorg. Chem. 1990, 29, 5006–5008 discloses syntheses of chelating bis(dioxaphospholane) ligands through chlorodioxaphospholane intermediates and the demonstration of catalytic competence of bis(phosphite) rhodium cations. A complex derived from dihydrobenzoin was tested as a precursor in the hydroformylation of olefins but gave a racemic mixture of aldehyde products.

Takaya, H., et al, J. Am. Chem. Soc. 1993, 115, 7033 reported the use of the mixed phosphine-phosphite ligand, BINAPHOS, for use in rhodium catalyzed hf. Enantioselectivities as high as 96% were observed for styrene hydroformylation, although the regioselectivity (branched/linear) was relatively low. Lanbers-Verstappen, M. H. L and de Vries. J. G, Adv. Synth. Catal. 2003, 345, 478–482 report application of BINAPHOS for the hydroformylation of allyl cyanide; this process was only moderately selective, giving chiral aldehyde product of 66% ee and a branched/linear ratio of 72:28. Mixed phosphine-phosphite ligands are more difficult to synthesize than their symmetrical counterparts.

U.S. Pat. No. 5,491,266 to Union Carbide discloses highly effective chiral bisphosphite ligands for use in asymmetric hf. Ligands prepared from optically active diols which bridge two phosphorus atoms were especially useful for a variety of olefin substrates. Preferred ligands, for example the prototype ligand known as Chiraphite, were prepared from optically active 2R,4R-pentanediol and substituted biphenols. The highest regioselectivities and enantioselectivities (>85% ee) were observed with vinylarene substrates. Other substrates were hydroformylated with lesser selectivities.

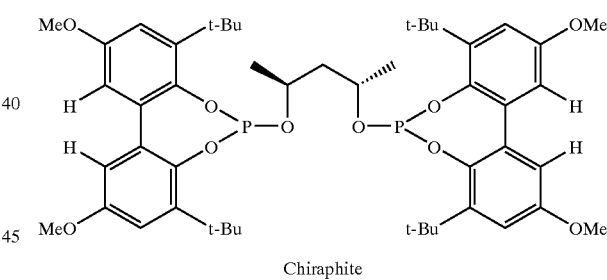

Chiraphite

Bisphosphite ligands described in U.S. Pat. No. 5,491,266 all contain optically active diolate moieties in the bridging positions. The biphenyl groups adopt non-planar, chiral conformations which can interconvert via rotation about the biaryl bond. van Leeuwen (Organometallics, 1997, 16, 2929) studied the effect of matching of the configuration of the bridging optically active diol with the configuration of the biaryl unit by using configurationally stable binaphthol as an additional optically active component. The resulting optically active bisphosphite diastereomers exhibited significant differences in catalyst activity, regioselectivity and enantioselectivity. The authors concluded that "both the absolute configuration of the 2,4-pentanediol ligand backbone and the chiral bisnaphthol substituents determine the stability and catalytic (performance) of the rhodium complexes". Similar results were reported by Bakos, J. et al, Canadian Journal of Chemistry, 2001, 79, 725, using platinum-tin catalysts with bisphosphite ligands prepared from optically active bridging diols and optically active bisnaphthols.

The search for more effective asymmetric hydroformylation processes is a constant one in the art. It would be desirable if asymmetric hf processes could be provided having good yields of optically active products without the need for optical resolution. It would be further desirable if asymmetric hf processes could be provided having the characteristics of high stereoselectivity, high regioselectivity, and good reaction rate. An additional desirable feature is the ability to easily synthesize a large number of structurally diverse catalysts for use with a variety of different olefin substrates, especially substrates that hitherto have not been reported to give synthetically useful results in terms of reactivity, product yield, regio- and stereo selectivity. Such substrates include, without limitation, vinyl acetate and allyl cyanide A further additional desirable feature is that synthetic routes used to prepare catalysts are readily amenable to scale up in cost-effective manner, to facilitate industrial applications.

SUMMARY OF THE INVENTION

One aspect of the present invention relates to a process for asymmetric hydroformylation in which a prochiral or chiral compound is contacted in the presence of an optically active metal-ligand complex catalyst to produce an optically active aldehyde or product derived from an optically active aldehyde, wherein the ligand is a novel compound as defined below as formula (1).

The processes of this invention are distinctive in that they provide good yields of optically active products having high stereoselectivity, high regioselectivity, and good reaction rate without the need for optical resolution. The processes of this invention enantioselectively produce a chiral center. An advantage of this invention is that optically active products can be synthesized from optically inactive reactants. Another advantage is that yield losses associated with the production of an undesired enantiomer can be substantially reduced.

The asymmetric syntheses processes of this invention are useful for the production of numerous optically active organic compounds, e.g., aldehydes, alcohols, ethers, esters, amines, amides, carboxylic acids and the like, which have a wide variety of applications.

Another aspect of the present invention relates to novel optically active ligands having the formula (1).

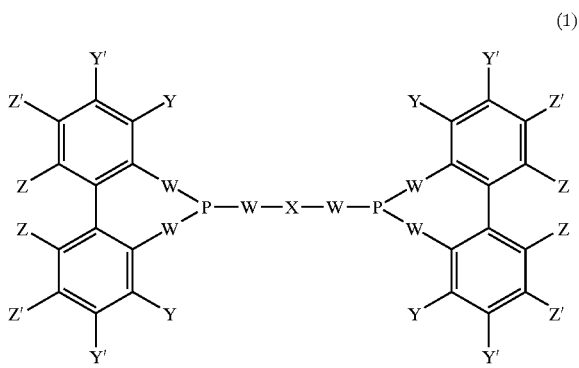

(1)

wherein each W is independently either oxygen or alkylamido (—NR), arylamido (—NAr), silylamido (—NSiR$_3$) or —NH; each Z and Y is the same or different and is a substituent other than hydrogen; each Z' and Y' is the same or different and is selected from hydrogen, substituents connected to the biaryl moieties through carbon, nitrogen, oxygen, or silicon, and halogen; Z and Z' can be optionally bridged to form a substituted or unsubstituted cyclic hydrocarbon residue; X is a substituted or unsubstituted hydrocarbon residue such that the corresponding HW—X—WH is not optically active. The substituted biaryl portion of the ligand is optically active.

This invention further relates to optically active metal-ligand complex catalysts comprising a metal complexed with an optically active ligand of formula (1).

This invention yet further relates to optically active products produced by the asymmetric syntheses of this invention.

DETAILED DESCRIPTION

The subject invention relates to asymmetric hydroformylation which involves the use of an optically active metal-phosphorus ligand complex catalyst and optionally free ligand of formula (1) in the production of optically active aldehydes wherein a prochiral or chiral olefinic compound is reacted with carbon monoxide and hydrogen. The optically active aldehydes produced correspond to the compounds obtained by the addition of a carbonyl group to an olefinically unsaturated carbon atom in the starting material with simultaneous saturation of the olefinic bond. The processing techniques of this invention may correspond to any of the known processing techniques heretofore employed in conventional hydroformylation reactions.

For instance, the asymmetric hf processes can be conducted in continuous, semi-continuous or batch fashion and involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

In general, the asymmetric hf reactions are carried out in a liquid reaction medium that contains a solvent for the optically active catalyst, preferably one in which the reaction ingredients including catalyst are substantially soluble. Alternatively, the reaction may be carried out in a neat liquid olefin in the absence of additional, unreactive solvent.

Illustrative olefin starting material reactants useful in certain of the asymmetric hf processes of this invention include those which can be terminally or internally unsaturated and be of straight chain, branched-chain or cyclic structure. Such olefins can contain from 4 to 40 carbon atoms or greater and may contain one or more ethylenic unsaturated groups. Moreover, such olefins may contain groups or substituents which do not essentially adversely interfere with the asymmetric hf process such as carbonyl, carbonyloxy, oxy, hydroxy, oxycarbonyl, cyano, halogen, alkoxy, aryl, haloalkyl, and the like. Illustrative olefinic unsaturated compounds include substituted and unsubstituted terminal olefins, internal olefins, alkyl alkenoates, alkenyl alkanoates, alkenyl alkyl ethers, alkenols and the like, e.g., 1-butene, 1-pentene, 1-hexene, 1-octene, 1-decene, 1-dodecene, 1-octadecene, 2-butene, isoamylene, 2-pentene, 2-hexene, 3-hexene, 2-heptene, cyclohexene, propylene dimers, propylene trimers, propylene tetramers, 2-ethylhexene, 3-phenyl-1-propene, 1,4-hexadiene, 1,7-octadiene, 3-cyclohexyl-1-butene, allyl alcohol, hex-1-en-4-ol, oct-1-en-4-ol, vinyl acetate, allyl acetate, 3-butenyl acetate, vinyl propionate, allyl propionate, allyl butyrate, methyl methacrylate, 3-butenyl acetate, vinyl ethyl ether, vinyl methyl ether, allyl ethyl ether, n-propyl-7-octenoate, 3-butenenitrile, 5-hexenamide, styrene, norbornene, alpha-methylstyrene and the like. Illustrative preferred olefinic unsaturated compounds include, for example, p-isobutylstyrene, 2-vinyl-6-methoxynaphthylene, phenyl vinyl ether, vinyl chloride, allyl cyanide, vinyl acetate, alpha-(p-trifluoromethylphenoxy)styrene and the like. Of course, it is understood that mixtures of different olefinic starting materials can be employed, if desired, by the asymmetric hf processes of the subject invention. More preferably, the subject invention is especially useful for the production of optically active aldehydes, by hydroformylating terminal olefins containing from 4 to 40 carbon atoms or greater and internal olefins containing from 4 to 40 carbon atoms or greater as well as starting material mixtures of such alpha olefins and internal olefins.

Illustrative prochiral and chiral olefins useful in the processes of this invention include those represented by the formula

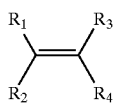

wherein $R_1$, $R_2$, $R_3$ and $R_4$ are the same or different (provided $R_1$ is different from $R_2$ or $R_3$ is different from $R_4$) and are selected from hydrogen; alkyl; substituted alkyl said substitution being selected from amino, including alkylamino and dialkylamino such as benzylamino and dibenzylamino, hydroxy, alkoxy such as methoxy and ethoxy, acyloxy such as acetoxy, halo, nitro, nitrile, thio, carbonyl, carboxamide, carboxaldehyde, carboxyl, carboxylic ester; aryl including phenyl; substituted aryl including phenyl said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio, said aryl substitution being less than 4 substituents; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto.

It is understood that the prochiral and chiral olefins of this definition also include molecules of the above general formula where the R-groups are connected to form cyclic compounds, e.g., 3-methyl-1-cyclohexene, and the like.

The optically active catalyst useful in this invention includes an optically active metal-ligand complex catalyst in which the ligand is optically active, preferably optically pure. The permissible metals which make up the optically active metal-ligand complexes include Group VIII metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium and ruthenium, especially rhodium. Other permissible metals include Group IB metals selected from copper (Cu), Silver (Ag), gold (Au) and mixtures thereof, and also Group VIB metals selected from chromium (Cr), molybdenum (Mo), tungsten (W) and mixtures thereof. Mixtures of metals from Group VIII, Group IB and Group VIB may be used in this invention. It is to be noted that the successful practice of this invention does not depend and is not predicated on the exact structure of the optically active metal-ligand complex species, which may be present in their mononuclear, dinuclear and or higher nuclearity forms, provided the ligand is optically active. Indeed, the exact optically active structure is not known.

The term "complex" as used herein and in the claims means a coordination compound formed by the union of one or more electronically rich molecules or atoms capable of independent existence with one or more electronically poor molecules or atoms, each of which is also capable of independent existence. For example, the preferred optically active ligands employable herein, i.e., phosphorus ligands, may possess one or more phosphorus donor atoms, each having one available or unshared pair of electrons which are each capable of forming a coordinate covalent bond independently or possibly in concert (e.g., via chelation) with the metal. As can be surmised from the above discussions, carbon monoxide (which is also properly classified as ligand) can also be present and complexed with the metal. The ultimate composition of the optically active complex catalyst may also contain an additional ligand, e.g., hydrogen or an anion satisfying the coordination sites or nuclear charge of the metal. It is of course to be understood that the optically active complex species is preferably free of any additional organic ligand or anion that might poison the catalyst and have an undue adverse effect on catalyst performance. It is preferred in the rhodium catalyzed asymmetric hydroformylation reactions of this invention that the active catalysts be free of halogen and sulfur directly bonded to the rhodium, although such may not be absolutely necessary.

The number of available coordination sites on such metals is well known in the art. Thus the optically active species may comprise a complex catalyst mixture, in their monomeric, dimeric or higher nuclearity forms, which are preferably characterized by at least one phosphorus-containing molecule complexed per one molecule of rhodium. As noted above, it is considered that the optically active species of the preferred rhodium catalyst employed in this invention during asymmetric hydroformylation may be complexed with carbon monoxide and hydrogen in addition to the optically active phosphorus ligands in view of the carbon monoxide and hydrogen gas employed by the asymmetric hydroformylation process.

Moreover, regardless of whether one preforms the optically active complex catalyst prior to introduction into the reaction zone or whether the active species is prepared in situ during the reaction, the asymmetric hydroformylation reaction may be effected in the presence of free ligand, although such may not be absolutely necessary.

This invention also relates to the aforementioned optically active ligands having the formula (1)

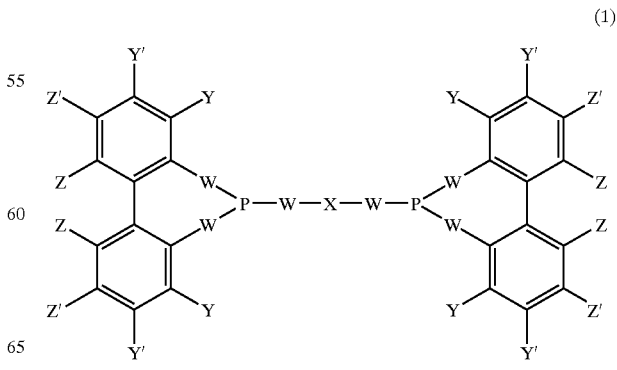

wherein each W is independently either oxygen or alkylamido (—NR), arylamido (—NAr), silylamido (—NSiR₃) or —NH; each Z and Y is the same or different and is a substituent other than hydrogen; Z', Y and Y' are the same or different and are selected from hydrogen, substituents connected to the biaryl moieties through carbon, nitrogen, oxygen, or silicon, and halogen; Z and Z' can be optionally bridged to form a substituted or unsubstituted cyclic hydrocarbon residue; X is a substituted or unsubstituted hydrocarbon residue such that the corresponding HW—X—WH is not optically active. The substituted biaryl portion of the ligand is optically active.

Of course, it is to be further understood that the biaryl moieties in the above formulae may also be substituted with any substituent radical that does not unduly adversely affect the processes of this invention. Illustrative substituents include radicals containing from 1 to 18 carbon atoms such as alkyl, aryl, aralkyl, alkaryl and cycloalkyl radicals; alkoxy radicals; silyl radicals such as —SiR₃ and —Si (OR)₃; amino radicals such as —NR₂; acyl radicals such as —C(O)R; acyloxy radicals such as —OC(O)R; carbonyloxy radicals such as —COOR; amido radicals such as —C(O) NR2 and —N(R)COR; sulfonyl radicals such as —SO₂ R; sulfinyl radicals such as —SOR₂; thionyl radicals such as —SR; phosphonyl radicals such as —P(O)R₂; as well as halogen, nitro, cyano, trifluoromethyl and hydroxy radicals and the like, wherein each R can be a monovalent hydrocarbon radical such as alkyl, aryl, alkaryl, aralkyl and cycloalkyl radicals, with the provisos that in amino substitutents such as —NR₂, each R taken together can also comprise a divalent bridging group that forms a heterocyclic radical with the nitrogen atom, in amido substituents such as —C(O)NR₂ and —N(R)COR, each R bonded to N can also be hydrogen, and in phosphonyl substituents such as —P(O) R₂, one R can be hydrogen. It is to be understood that each R group in a particular substituent may be the same of different. Such hydrocarbon substituent radicals could possibly in turn be substituted with a substituent such as already herein outlined above provided that any such occurrence would not unduly adversely effect the processes of this invention. At least one ionic moiety selected from salts of carboxylic acid and of sulfonic acid may be substituted on an aryl moiety in the above formulae.

Illustrative monovalent hydrocarbon residues represented by the Z, Z', Y and Y' groups in the above formulae include substituted or unsubstituted monovalent hydrocarbon radicals containing from 1 to 30 carbon atoms selected from substituted or unsubstituted alkyl, aryl, alkaryl, aralkyl and alicyclic radicals. While each Z, Z', Y and Y' groups in a given formula may be individually the same or different, preferably they are the same for each biaryl moiety.

More specific illustrative monovalent hydrocarbon residues represented by Z, Z', Y and Y' include primary, secondary and tertiary chain alkyl radicals such as methyl, ethyl, propyl, isopropyl, butyl, sec-butyl, t-butyl, neo-pentyl, sec-amyl, t-amyl, iso-octyl, 2-ethylhexyl, iso-nonyl, iso-decyl, octadecyl and the like; aryl radicals such as phenyl, naphthyl, anthracyl and the like; aralkyl radicals such as benzyl, phenylethyl and the like; alkaryl radicals such as tolyl, xylyl, p-alkylphenyls and the like; and alicyclic radicals such as cyclopentyl, cyclohexyl, cyclooctyl, cyclohexylethyl, 1-methylcyclohexyl and the like. Preferably the unsubstituted alkyl radicals may contain from 1 to 18 carbon atoms, more preferably from 1 to 10 carbon atoms, while the unsubstituted aryl, aralkyl, alkaryl and alicyclic radicals preferably contain from 6 to 18 carbon atoms. Among the more preferred Z, Z', Y and Y' residues are tert-butyl radicals.

Moreover, the above-described radicals represented by Z, Z', Y and Y' of the above formulae, may be further substituted with any substituent that does not unduly adversely effect the desired results of this invention. Illustrative substituents are, for example, monovalent hydrocarbon radicals having between one and about 18 carbon atoms, such as alkyl, aryl, alkaryl, aralkyl, cycloalkyl and other radicals as defined above. In addition, various other substituents that may be present include, e.g., halogen, preferably chlorine or fluorine, —NO2, —CN, —CF3, —OH, —Si(CH3)3, —Si (OCH3) 3, —Si(C3 H7)3, —C(O)CH3, —C(O)C2 H5, —OC(O)C6 H5, —C(O)OCH3, —N(CH3)2, —NH2, —NHCH3, —NH(C2 H5), —CONH2, —CON(CH3) 2, —S(O)2 C2 H5, —OCH3, —OC2 H5, —OC. sub. 6 H5, —C(O)C6 H5, —O(t-C4 H9), —SC 2 H. sub.5, —OCH2 CH2 OCH3, —(OCH2 CH2)2 OCH. sub.3, —(OCH2 CH2)3 OCH3, —SCH3, —S(O)CH. sub.3, —SC6 H5, —P(O}(C6 H5)2, —P(O)(CH 3)2, —P(O)(C2 H5)2, —P(O)(C3 H. sub.7)2, —P(O)(C4 H9)2, —P(O)(C6 H13). sub.2, —P(O)CH. sub.3 (C6 H5), —P(O)(H)(C6 H5), —NHC(O)CH3 and the like. Moreover, each Z, Y, Ar, Y' and Y" group may contain one or more such substituent groups which may also be the same or different in any given ligand molecule. Preferred substituent radicals include alkyl and alkoxy radicals containing from 1 to 18 carbon atoms and more preferably from 1 to 10 carbons.

Illustrative but non-limiting examples of preferred optically active ligands include:

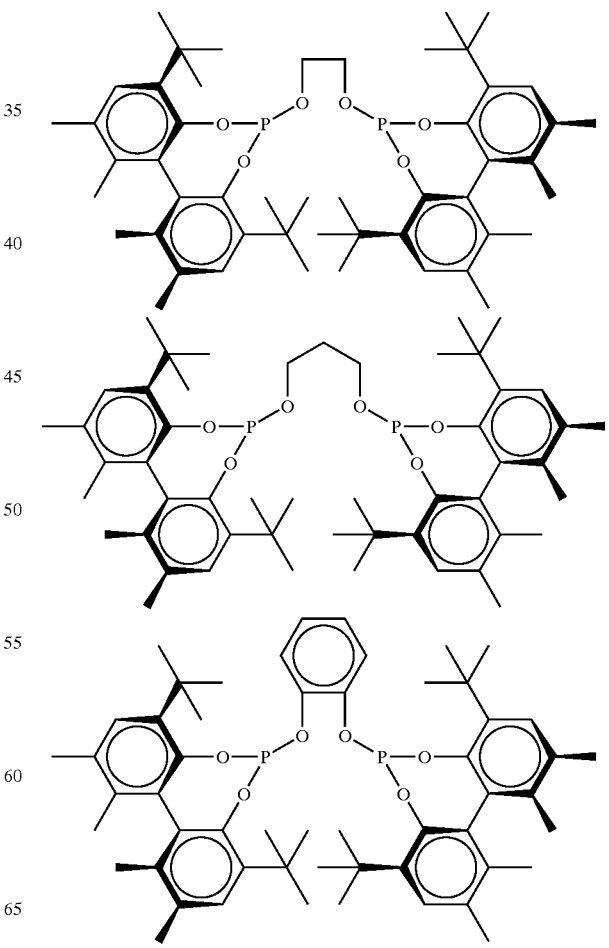

-continued
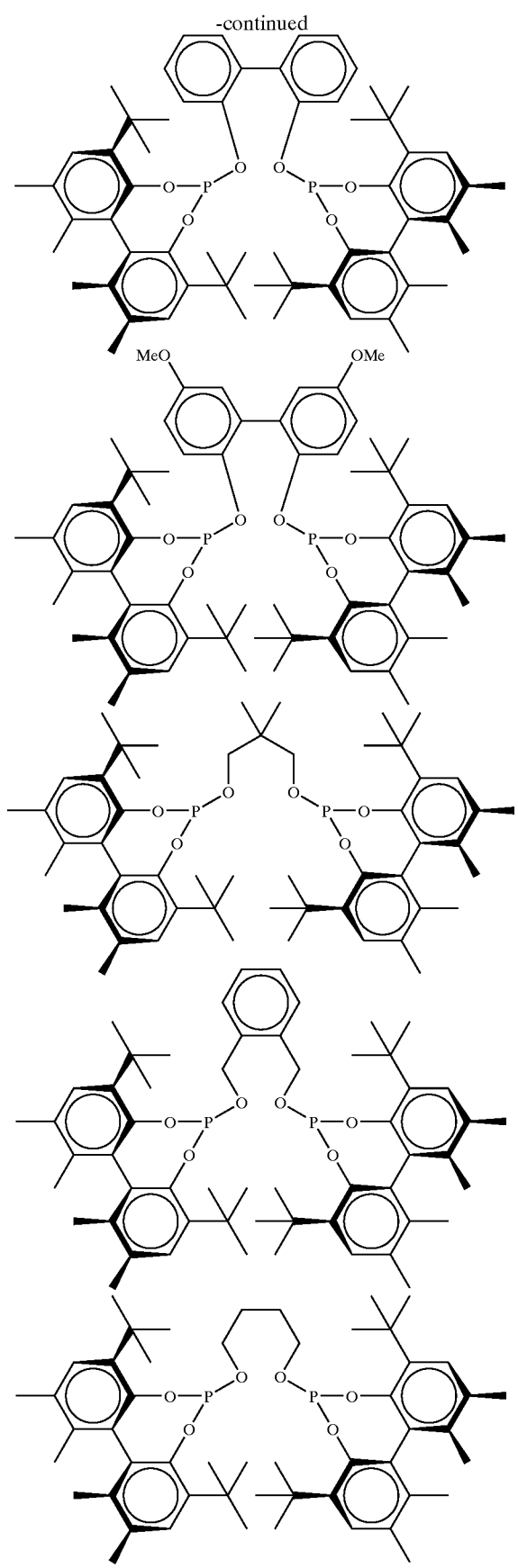
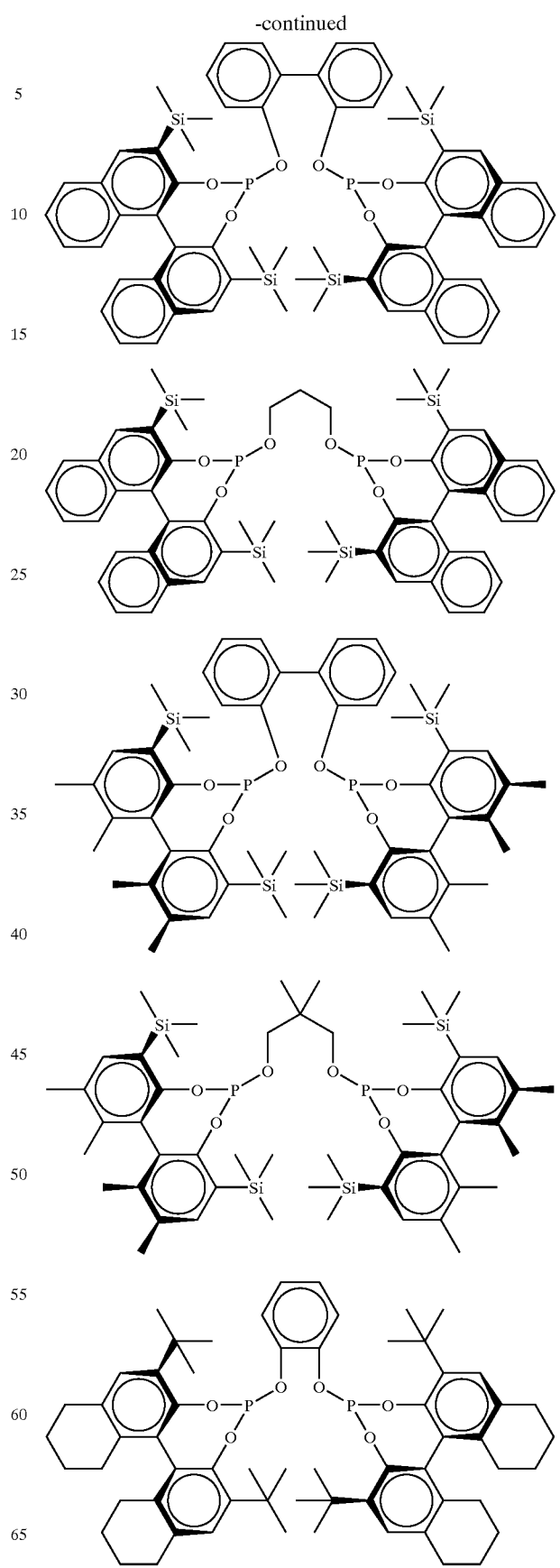

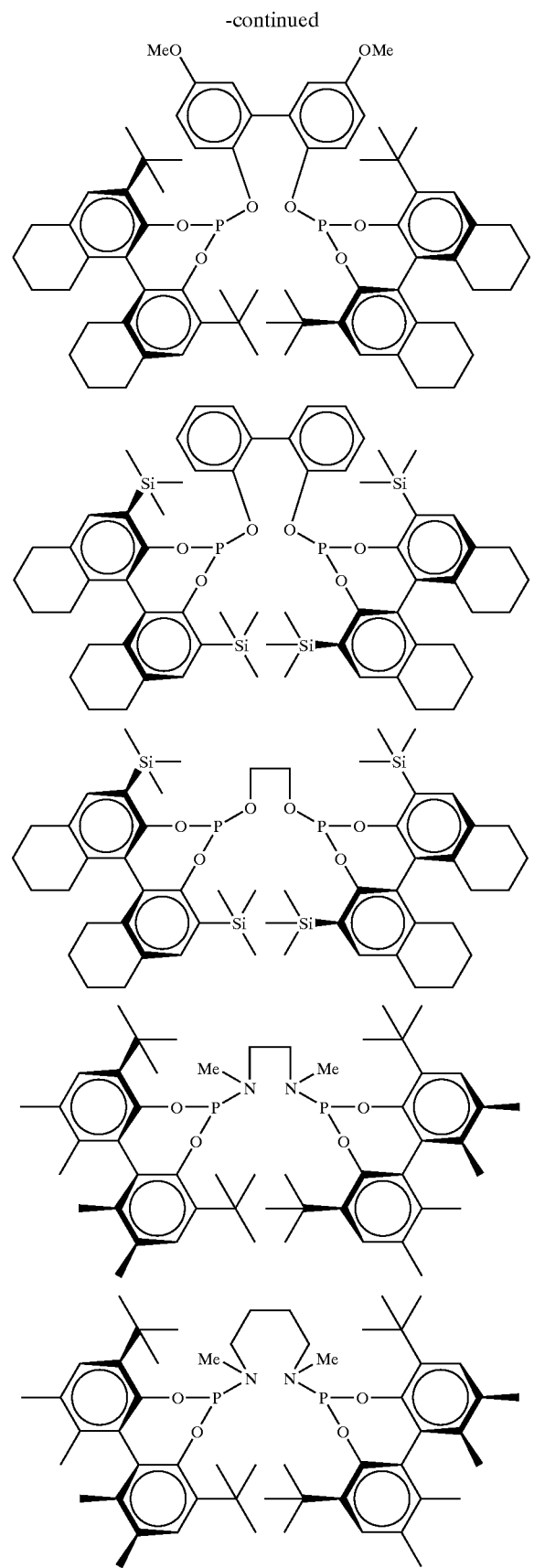
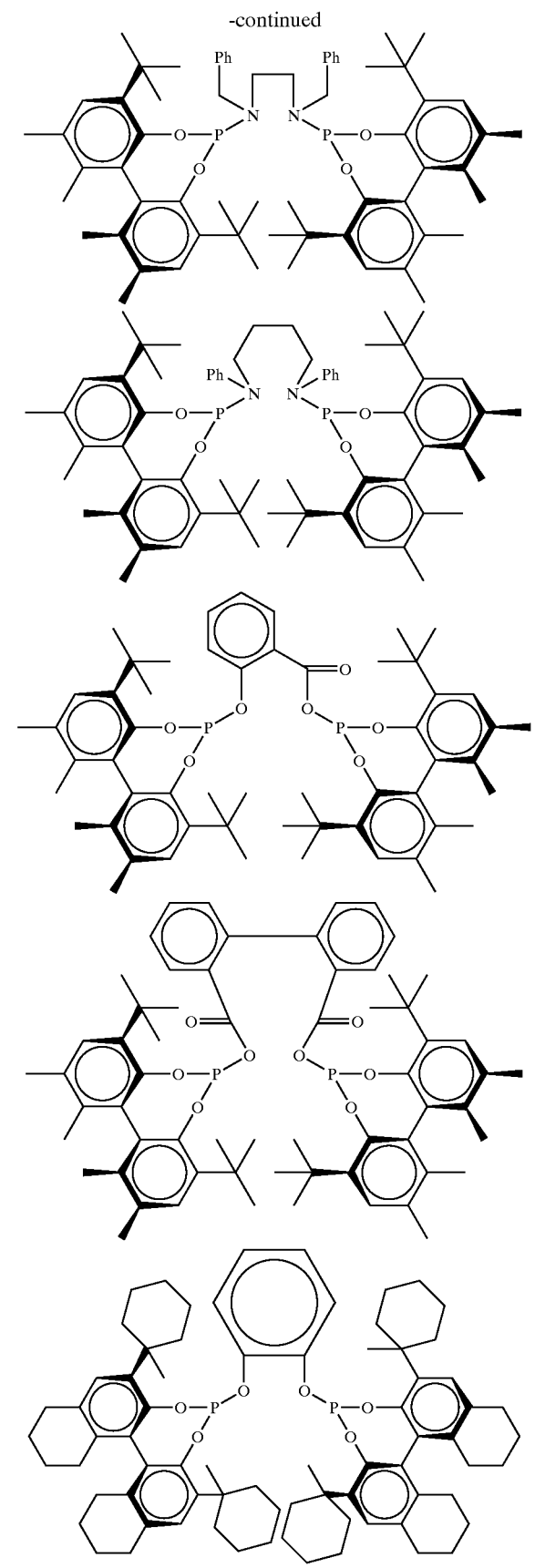

-continued

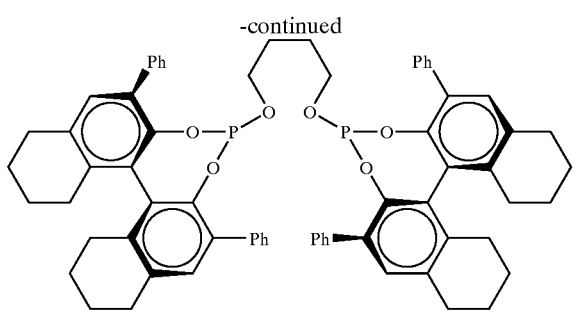

The optically active ligands employed in the complex catalysts of this invention are uniquely adaptable and suitable for asymmetric hf. For instance, the optically active phosphorus ligands may provide very good rhodium complex stability in addition to providing good catalytic activity for the asymmetric hydroformylation of all types of permissible olefins. Further, their unique chemical structure should provide the ligand with very good stability against side reactions such as being hydrolyzed during asymmetric hydroformylation, as well as upon storage.

The types of novel optically active ligands of the generic class employable in this invention can be prepared by methods known in the art. For instance, the optically active phosphorus ligands employable in this invention can be prepared via a series of conventional phosphorus halide-alcohol or amine condensation reactions in which at least one of the alcohol or amine ingredients is optically active or optically pure. Such types of condensation reactions and the manner in which they may be conducted are well known in the art. Moreover, the phosphorus ligands employable herein can be readily identified and characterized by conventional analytical techniques, such as Proton-1 and/or Phosphorus-31 nuclear magnetic resonance spectroscopy and Fast Atom Bombardment Mass Spectroscopy if desired.

As noted above, the optically active ligands can be employed as both the ligand of the optically active metal-ligand complex catalyst, as well as, the free ligand that can be present in the reaction medium of the processes of this invention. In addition, it is to be understood that while the optically active ligand of the metal-ligand complex catalyst and any excess free ligand preferably present in a given process of this invention are normally the same type of ligand, different types of optically active ligands, as well as, mixtures of two or more different optically active ligands may be employed for each purpose in any given process, if desired.

The optically active metal-ligand complex catalysts of this invention may be formed by methods known in the art. See, for example, U.S. Pat. No. 5,491,266 and references therein. For instance, preformed metal hydrido-carbonyl catalysts may possibly be prepared and introduced into the reaction medium of an asymmetric syntheses process. More preferably, the metal-ligand complex catalysts of this invention can be derived from a metal catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction medium along with the ligand for the in situ formation of the active catalyst. In a preferred embodiment, rhodium dicarbonyl acetylacetonate is employed as a rhodium precursor and reacted in the presence of a solvent with a phosphorus ligand compound to form a catalytic rhodium-phosphorus complex precursor which is introduced into the reactor, optionally along with excess free phosphorus ligand, for the in situ formation of the active catalyst. In any event, it is sufficient for the purpose of this invention to understand that an optically active metal-ligand complex catalyst is present in the reaction medium under the conditions of the asymmetric hydroformylation process.

Moreover, it is clear in that the amount of optically active complex catalyst present in the reaction medium of a given process of this invention need only be that minimum amount necessary to provide the given metal concentration desired to be employed and which will furnish the basis for at least that catalytic amount of metal necessary to catalyze the particular asymmetric hf process desired. In general, metal concentrations in the range of from about 1 ppm to about 10,000 ppm, calculated as free metal, and ligand to metal mole ratios in the catalyst ranging from about 0.5:1 to about 200:1, should be sufficient for most asymmetric syntheses processes. Moreover, in the rhodium catalyzed asymmetric hydroformylation processes of this invention, it is generally preferred to employ from about 10 to 1000 ppm of rhodium and more preferably from 25 to 750 ppm of rhodium, calculated as free metal.

A further aspect of this invention can be described as the use in asymmetric hf of a catalyst precursor composition consisting essentially of a solubilized metal-ligand complex precursor catalyst, an organic solvent and free ligand. Such precursor compositions may be prepared by forming a solution of a metal starting material, such as a metal oxide, hydride, carbonyl or salt e.g., a nitrate, which may or may not be in complex combination with an optically active ligand, an organic solvent and a free ligand as defined herein. Any suitable metal starting material may be employed, e.g., rhodium dicarbonyl acetylacetonate, $Rh_2O_3$, $Rh_4(CO)_{12}$, $Rh_6(CO)_{16}$, $Rh(NO_3)_3$, bisphosphite rhodium carbonyl hydrides, iridium carbonyl, bisphosphite iridium carbonyl hydrides, osmium halide, chlorosmic acid, osmium carbonyls, palladium hydride, palladous halides, platinic acid, platinous halides, ruthenium carbonyls, as well as other salts of other metals and carboxylates of C2–C16 acids such as cobalt chloride, cobalt nitrate, cobalt acetate, cobalt octoate, ferric acetate, ferric nitrate, nickel fluoride, nickel sulfate, palladium acetate, osmium octoate, iridium sulfate, ruthenium nitrate, and the like. Of course, any suitable solvent may be employed such as those employable in the asymmetric hf process desired to be carried out. Alternatively, the reaction may be carried out in a neat liquid olefin in the absence of additional, unreactive solvent. The desired asymmetric hf process may of course also dictate the various amounts of metal, solvent and optically active ligand present in the precursor solution. Optically active ligands if not already complexed with the initial metal may be complexed to the metal either prior to or in situ during the asymmetric syntheses process.

By way of illustration, since the preferred metal is rhodium and the preferred optically active ligand is a phosphorus ligand, a preferred catalyst precursor composition of this invention can include a solubilized rhodium carbonyl phosphorus complex precursor catalyst, an organic solvent and phosphorus ligand prepared by forming a solution of rhodium dicarbonyl acetylacetonate, an organic solvent and optically active phosphorus ligand as defined herein. The phosphorus readily replaces one or both of the carbonyl ligands of the rhodium-acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium phosphorus complex precursor are soluble can be employed. Accordingly, the amounts of rhodium complex catalyst precursor, organic solvent and optically active phosphorus ligand as well as their preferred embodiments present in such catalyst precursor compositions may obviously correspond to those amounts employable in the asymmetric hydroformylation process of this invention and which have already been discussed herein. It is believed that the acetylacetonate ligand of the precursor catalyst is replaced after the asymmetric hydroformylation process has begun with a different ligand, e.g., hydrogen or carbon monoxide, to form the optically active rhodium complex catalyst as explained above. The acetylacetone which is freed from the precursor catalyst under hydroformylation conditions may be removed from the reaction medium with the product aldehyde and thus is in no way detrimental to the asymmetric hydroformylation process. The use of such preferred rhodium complex catalytic precursor compositions thus provides a simple economical and efficient method of handling the rhodium precursor metal and hydroformylation start-up.

The optically active catalyst may optionally be supported. Advantages of a supported catalyst may include ease of catalyst separation and ligand recovery. Illustrative examples of supports include alumina, silica gel, ion-exchange resins, polymeric supports and the like.

The reaction conditions of effecting the asymmetric hydroformylation process of this invention may be those heretofore conventionally used and may comprise a reaction temperature of from about −25.degree. C. or lower to about 200.degree. C. and pressures ranging from about 1 to 10,000 psia. Moreover, asymmetric hf reactions may be performed at lower temperatures than normally preferred to more effectively increase product enantioselectivity.

As noted, the preferred process of this invention involves the production of optically active aldehydes via asymmetric hydroformylation of a prochiral or chiral olefinic unsaturated compound with carbon monoxide and hydrogen in the presence of an optically active metal-phosphorus ligand complex catalyst and optionally free phosphorus ligand, especially an optically active rhodium-phosphorus ligand complex catalyst.

Of course, it is to be understood that while the optimization of the reaction conditions necessary to achieve the best results and efficiency desired are dependent upon one's experience in the utilization of the subject invention, only a certain measure of experimentation should be necessary to ascertain those conditions which are optimum for a given situation and such should be well within the knowledge of one skilled in the art and easily obtainable by following the more preferred aspects of this invention as explained herein and/or be simple routine experimentation.

For instance, the total gas pressure of hydrogen and carbon monoxide of the asymmetric hydroformylation process of this invention may range from about 1 to about 10,000 psia. More preferably, however, in the asymmetric hydroformylation of prochiral olefins to produce optically active aldehydes, it is preferred that the process be operated at a total gas pressure of hydrogen and carbon monoxide of less than about 1500 psia, and more preferably less than about 1000 psia. The minimum total pressure of the reactants is not particularly critical and is limited predominately only by the amount of reactants necessary to obtain a desired rate of reaction. In general, the molar ratio of gaseous hydrogen to carbon monoxide may range from about 1:10 to 100:1 or higher, the more preferred hydrogen to carbon monoxide molar ratio being from about 1:1 to about 1:10. Higher molar ratios of carbon monoxide to gaseous hydrogen may generally tend to favor higher branched/normal ratios.

Further as noted above, the preferred asymmetric hydroformylation process of this invention may be conducted at a reaction temperature from about −25.degree. C. or lower to about 200. degree. C. The preferred reaction temperature employed in a given process will of course be dependent upon the particular olefinic starting material and optically active metal-ligand complex catalyst employed as well as the efficiency desired. Lower reaction temperatures may generally tend to favor higher enantiomeric excesses (ee) and branched/normal ratios. In general, asymmetric hydroformylations at reaction temperatures of about 0.degree. C. to about 120.degree. C. are preferred for all types of olefinic starting materials. More preferably, alpha-olefins can be effectively hydroformylated at a temperature of from about 0.degree. C. to about 90. degree. C. while even less reactive olefins than conventional linear alpha-olefins and internal olefins as well as mixtures of alpha-olefins and internal olefins are effectively and preferably hydroformylated at a temperature of from about 25.degree. C. to about 120.degree. C. Indeed, in the rhodium-catalyzed asymmetric hydroformylation process of this invention, no substantial benefit is seen in operating at reaction temperatures much above 120.degree. C. and such is considered to be less desirable.

The processes are conducted for a period of time sufficient to produce the optically active products. The exact reaction time employed is dependent, in part, upon factors such as temperature, nature and proportion of starting materials, and the like. The reaction time will normally be within the range of from about one-half to about 200 hours or more, and preferably from less than about one to about 10 hours.

As outlined herein, the asymmetric hf process of this invention can be carried out in either the liquid or gaseous state and involve a batch, continuous liquid or gas recycle system or combination of such systems. A batch system is preferred for conducting the processes of this invention. Preferably, asymmetric hydroformylation of this invention involves a batch homogeneous catalysis process wherein the hydroformylation is carried out in the presence of both free phosphorus ligand and any suitable conventional solvent as further outlined herein.

The asymmetric hydroformylation process of this invention may be conducted in the presence of an organic solvent for the optically active metal-ligand complex catalyst. Depending on the particular catalyst and reactants employed, suitable organic solvents include, for example, alcohols, alkanes, alkenes, alkynes, ethers, aldehydes, ketones, esters, acids, amides, amines, aromatics and the like. Any suitable solvent which does not unduly adversely interfere with the intended asymmetric syntheses process can be employed and such solvents may include those heretofore commonly employed in known metal catalyzed processes. Increasing the dielectric constant or polarity of a solvent may generally tend to favor increased reaction rates. Of course, mixtures of one or more different solvents may be employed if desired. It is obvious that the amount of solvent employed is not critical to the subject invention and need only be that amount sufficient to provide the reaction medium with the particular metal concentration desired for a given process. In general, the amount of solvent when employed may range from about 5 percent by weight up to about 95 percent by weight or more based on the total weight of the reaction medium.

As noted above, the asymmetric hydroformylation process of this invention can be carried out in the presence of free ligand, i.e., ligand that is not complexed with the metal of the optically active metal-ligand complex catalyst employed. While it is preferred to employ a free ligand that is the same as the ligand of the metal-ligand complex catalyst such ligands need not be the same in a given process, but can be different if desired. While the asymmetric hydroformylation process of this invention may be carried out in any excess amount of free ligand desired, the employment of free ligand may not be absolutely necessary. Accordingly, in general, amounts of ligand of from about 2 to about 100, or higher if desired, moles per mole of metal (e.g., rhodium) present in the reaction medium should be suitable for most purposes, said amounts of ligand employed being the sum of both the amount of ligand that is bound (complexed) to the metal present and the amount of free (non-complexed) ligand present. Of course, if desired, make-up ligand can be supplied to the reaction medium of the asymmetric hydroformylation process, at any time and in any suitable manner, to maintain a predetermined level of free ligand in the reaction medium.

The ability to carry out the processes of this invention in the presence of free ligand can be a beneficial aspect of this invention in that it removes the criticality of employing very low precise concentrations of ligand that may be required of certain complex catalysts whose activity may be retarded when even any amount of free ligand is also present during the process, particularly when large scale commercial operations are involved, thus helping to provide the operator with greater processing latitude.

The optically active products of the process of this invention have a wide range of utility that is well known and documented in the prior art, e.g. they are especially useful as pharmaceuticals, flavors, fragrances, agricultural chemicals and the like. Illustrative therapeutic applications, include, for example, non-steroidal anti-inflammatory drugs, ACE inhibitors, beta-blockers, analgesics, bronchodilators, spasmolytics, antihistimines, antibiotics, antidepressants, antitumor agents and the like.

The processes of this invention can provide optically active chiral aldehyde products having very high enantioselectivity and regioselectivity. To be viable for commercial applications, it is essential that processes fulfill both of these selectivity criteria. Enantiomeric excesses of preferably greater than 50%, more preferably greater than 75% and most preferably greater than 90% can be obtained by the processes of this invention. Branched/linear molar ratios of preferably greater than 4:1, more preferably greater than 10:1 and most preferably greater than 20:1 can be obtained by the processes of this invention. Depending upon the structure of the prochiral olefin, the linear aldehyde product may be chiral, wherein linear/branched ratios of preferably greater than 4:1, more preferably greater than 10:1 and most preferably greater than 20:1 can be obtained by the processes of this invention. The processes of this invention can also be carried out at highly desirable reaction rates suitable for commercial use.

The desired optically active products, e.g., aldehydes, may be recovered in any conventional manner. Suitable separation techniques include, for example, solvent extraction, crystallization, distillation, vaporization, wiped film evaporation, falling film evaporation and the like. It may be desired to remove the optically active products from the reaction system as they are formed through the use of trapping agents as described in WO Patent 88/08835. The enantiomeric excess and/or branched/linear ration may be increased by recrystallization as described in U.S. Pat. No. 5,430,194, or by recrystallization of a derivative.

The optically active products produced by the asymmetric hf processes of this invention can undergo further reaction(s) to afford desired derivatives thereof. Such permissible derivatization reactions can be carried out in accordance with conventional procedures known in the art. Derivatization can be carried out either as a separate synthetic operation after isolation of the hf product or by an in situ process. For in situ derivatization, for example reduction or reductive amination, derivatization may be performed either subsequent to or concurrent with the asymmetric hydroformylation process. For optically active aldehydes prepared by asymmetric hydroformylation, illustrative derivatization reactions include, for example, oxidation to carboxylic acids, reduction to alcohols, aldol condensation, reductive amination to amines, amination to imines and the like. In addition, the optically active aldehyde produced by this invention may undergo intermolecular or intramolecular reaction with additional reactive functional groups which are present in the product. For example, aldehydes which are prepared via hydroformylation of olefins which contain pendant alcohol substituents, may undergo intramolecular cyclization to form chiral lactol derivatives. This invention is not intended to be limited in any manner by the permissible derivatization reactions.

As indicated above, the processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

In one preferred embodiment of the present allyl cyanide was subjected to asymmetric hydroformylation in the presence of, as catalyst, a rhodium complex of a ligand according to formula (1). A range of such catalysts were employed in screening experiments under unoptimized process conditions, to determine enantioselctivity (% ee), regioselectvity (b/l) and % conversion of substrate. Results are shown in table 1 (EXAMPLES section) alongside comparative examples in which Rh complexes of Chiraphite and BINAPHOS ligands are employed. These results, in particular

19

EXAMPLE 22 demonstrate the unexpected utility and superior performance of novel ligands of this invention, for this challenging hf substrate.

In another preferred embodiment of the present invention, vinyl acetate was subjected to asymmetric hydroformylation in the presence of, as catalyst, a rhodium complex of a ligand according to formula (1). A range of such catalysts were employed in screening experiments under unoptimized process conditions, to determine enantioselctivity (% ee), regioselectvity (b/l) and % conversion of substrate. Results are shown in table 1 (EXAMPLES section) alongside comparative examples in which Rh complexes of Chiraphite and BINAPHOS ligands are employed. These results, in particular EXAMPLES 30 and 36 demonstrate the unexpected utility and superior performance of novel ligands of this invention, for this challenging hf substrate.

As used herein, the following terms have the indicated meanings:

chiral—molecules which have one or more centers or axes of asymmetry and are not superimposable on their mirror images.

achiral—molecules or processes which do not exhibit optical activity.

prochiral—molecules which have the potential to be converted to a chiral product in a particular process.

chiral center—any structural feature of a molecule that is a site of asymmetry.

racemic—a 50/50 mixture of two enantiomers of a chiral compound.

stereoisomers—compounds which have identical chemical constitution, but differ as regards the arrangement of the atoms or groups in space.

enantiomers—stereoisomers which are non-superimposable mirror images of one another.

stereoselective—a process which produces a particular stereoisomer in favor of others.

enantiomeric excess (ee)—a measure of the relative amounts of two enantiomers present in a product. ee may be calculated by the formula [amount of major enantiomer−amount of minor enantiomer]/[amount of major enantiomer+amount of minor enantiomer].

optical activity—an indirect measurement of the relative amounts of stereoisomers present in a given product. Chiral compounds have the ability to rotate plane polarized light. When one enantiomer is present in excess over the other, the mixture is optically active.

optically active—a mixture of stereoisomers which rotates plane polarized light due to an excess of one of the stereoisomers over the others.

optically pure—a single stereoisomer which rotates plane polarized light.

regioisomers—compounds which have the same molecular formula but differing in the connectivity of the atoms.

regioselective—a process which favors the production of a particular regloisomer over all others.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

20

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

EXAMPLES

The following examples are provided to further illustrate the present invention.

Example 1

Preparation of R-(BIPHEN)PBr

R-BIPHEN-H$_2$ (obtained from Strem Chemical, 4.06 g, 11.45 mmol) was dissolved in 100 mL of toluene. Triethylamine (3.25 mL, 23.31 mmol) was added. Phosphorus tribromide (1.1 mL, 11.6 mmol) was added to the reaction mixture and then stirred for 18 hours. The suspension was filtered, and the filtrate was evaporated to give R-(BIPHEN) bromidite as a white solid (3.41 g, 7.87 mmol, 69% yield) having the structure:

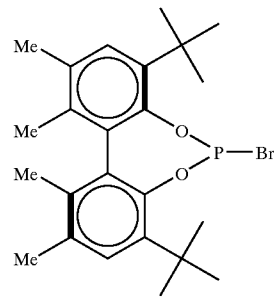

$^{31}P\{^{1}H\}$ NMR (C$_6$D$_6$) δ 184; $^1$H NMR (C$_6$D$_6$) δ 7.18 (s, 1H), 7.08 (s, 1H), 1.93 (s, 3H), 1.92 (s, 3H), 1.57 (s, 3H), 1.56 (s, 3H), 1.48 (s, 9H), 1.39 (s, 9H).

Example 2

Preparation of R-BIPHEN-biphenol-bisphosphite (I)

A solution of 2,2'-biphenol (212 mg, 1.14 mmol) and 300 μL Et$_3$N in 15 mL toluene was added to a solution of (R-BIPHEN)PBr (983 mg, 2.27 mmol) in 20 mL toluene. The solution was stirred for 18 h at ambient temperature and then filtered. The filtrate was evaporated to a white solid which was triturated with MeCN. The supernatant was decanted and the solid product was dried under vacuum (737 mg, 68% yield). $^{31}$P{$^{1}$H} NMR (C$_6$D$_6$) δ 134; $^{1}$H NMR (C$_6$D$_6$) δ 7.48 (dd, 2H), 7.31 (d, 2H), 7.25 (s, 2H), 7.23 (s, 2H), 7.03 (dt, 2H), 6.86 (dt, 2H), 2.17 (s, 6H), 2.09 (s, 6H), 1.83 (s, 6H), 1.76 (s, 6H), 1.49 (s, 18H), 1.46 (s, 18H). NMR characterization revealed the product to have the structure:

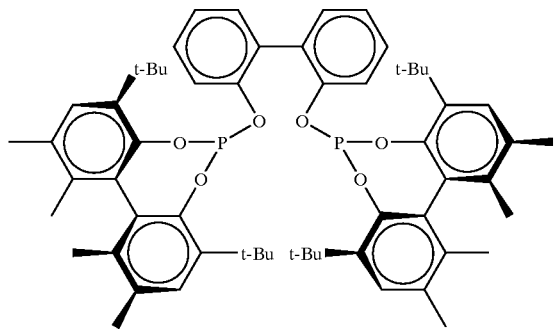

I

Example 3

Preparation of R-BIPHEN-ethylene glycol-bisphosphite (II)

A solution of ethylene glycol (36.6 mg, 0.589 mmol) and 240 μL Et$_3$N in 5 mL toluene was added to a solution of (R-BIPHEN)PBr (522 mg, 1.20 mmol) in 10 mL toluene. The solution was stirred for 18 h at ambient temperature and then filtered. The filtrate was evaporated to a colorless oil which was triturated with MeCN. The supernatant was decanted and the oily solid product was dried under vacuum (480 mg, 98% yield). NMR characterization revealed the product to have the structure:

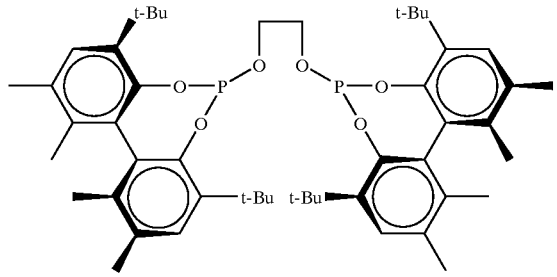

II

Example 4

Preparation of R-BIPHEN-neopentyl glycol-bisphosphite (III)

A solution of neopentyl glycol (71.0 mg, 0.68 mmol) and 260 μL Et$_3$N in 5 mL toluene was added to a solution of (R-BIPHEN)PBr (583 mg, 1.34 mmol) in 10 mL toluene. The solution was stirred for 2 h at ambient temperature and then filtered. The filtrate was evaporated to a white solid which was dried under vacuum (0.59 g, 99% yield). NMR characterization revealed the product to have the structure:

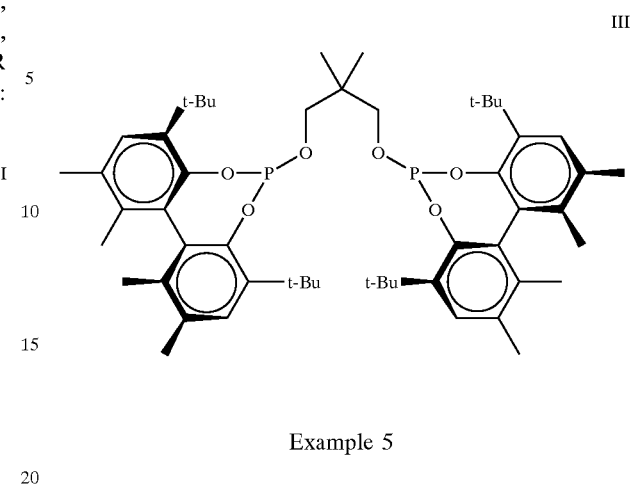

III

Example 5

Preparation of R-BIPHEN-(N-Me-diethanolamine)-bisphosphite (IV)

A solution of N-Me-diethanolamine (77.8 mg, 0.653 mmol) and 300 μL Et$_3$N in 5 mL toluene was added to a solution of (R-BIPHEN)PBr (550 mg, 1.27 mmol) in 10 mL toluene. The solution was stirred for 18 h at ambient temperature and then filtered. The filtrate was evaporated to a white solid which was dried under vacuum (425 mg, 74% yield). NMR characterization revealed the product to have the structure:

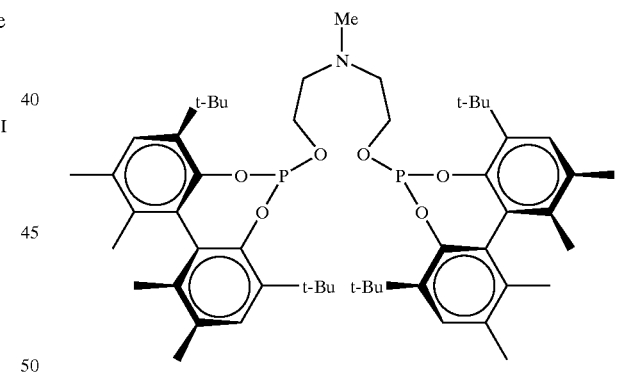

IV

Example 6

Preparation of R-BIPHEN-(1,2-benzenedimethanol)-bisphosphite (V)

A solution of 1,2-benzenedimethanol (82.5 mg, 0.598 mmol) and 240 μL Et$_3$N in 5 mL toluene was added to a solution of (R-BIPHEN)PBr (527 mg, 1.22 mmol) in 10 mL toluene. The solution was stirred for 2.5 h at ambient temperature and then filtered. The filtrate was evaporated to a colorless solid which was dried under vacuum (0.543 g, 49% yield). NMR characterization revealed the product to have the structure:

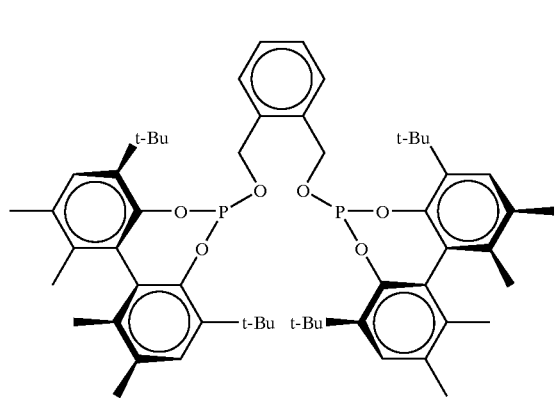

V

Example 7

Preparation of R-BIPHEN-(2,2'-biphenyldimethanol)-bisphosphite (VI)

A solution of 2,2'-biphenyldimethanol (147.1 mg, 0.686 mmol) and 240 μL Et₃N in 5 mL toluene was added to a solution of (R-BIPHEN)PBr (596 mg, 1.38 mmol) in 10 mL toluene. The solution was stirred for 3.5 h at ambient temperature and then filtered. The filtrate was evaporated to a white solid which was dried under vacuum (0.670 g, 98% yield). NMR characterization revealed the product to have the structure:

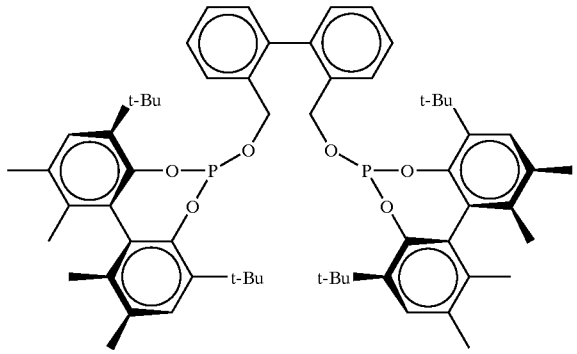

VI

Example 8

Preparation of R-BIPHEN-1,3-propanediol-bisphosphite (VII)

A solution of 1,3-propanediol (46.0 mg, 0.604 mmol) and 220 μL Et₃N in 5 mL toluene was added to a solution of (R-BIPHEN)PBr (524 mg, 1.21 mmol) in 10 mL toluene. The solution was stirred for 18 h at ambient temperature and then filtered. The filtrate was evaporated to a white solid which was dried under vacuum (0.500 g, 98% yield). NMR characterization revealed the product to have the structure:

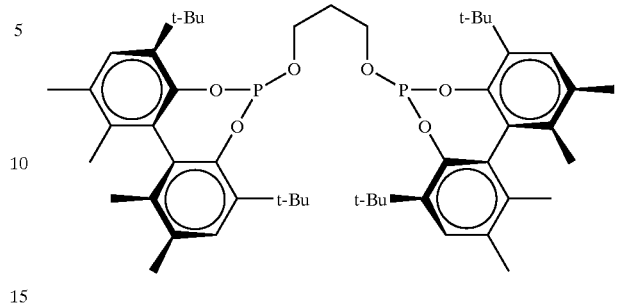

VII

Example 9

Preparation of R-BIPHEN-(1,1'-methylenebinaphthol)-bisphosphite (VIII)

A solution of 1,1'-methylenebinaphthol (208.0 mg, 0.692 mmol) and 240 μL Et₃N in 10 mL toluene was added to a solution of (R-BIPHEN)PBr (606 mg, 1.40 mmol) in 10 mL toluene. The solution was stirred for 18 h at ambient temperature and then filtered. The filtrate was evaporated to a pink solid which was triturated with 8 mL of MeCN to yield a white solid which was dried under vacuum (0.688 g, 93% yield). NMR characterization revealed the product to have the structure:

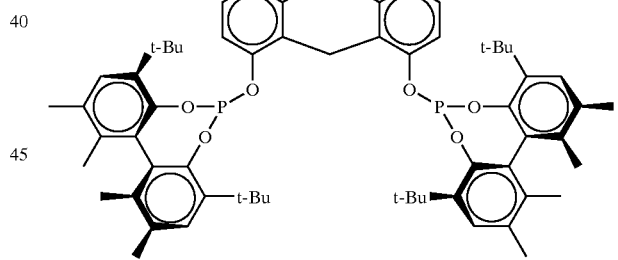

VIII

Example 10

Preparation of (R-BIPHEN)-2,2'-methylenebis(4-chlorophenol)bisphosphite (IX)

A solution of 1,1'-methylene-5,5'-dichlorobisphenol (185 mg, 0.687 mmol) and 240 μL Et₃N in 10 mL toluene was added to a solution of (R-BIPHEN)PBr (589 mg, 1.36 mmol) in 10 mL toluene. The solution was stirred for 4 h at ambient temperature and then filtered. The filtrate was evaporated to a white solid which was triturated with MeCN to yield a white solid which was dried under vacuum (0.533 g, 75% yield). NMR characterization revealed the product to have the structure:

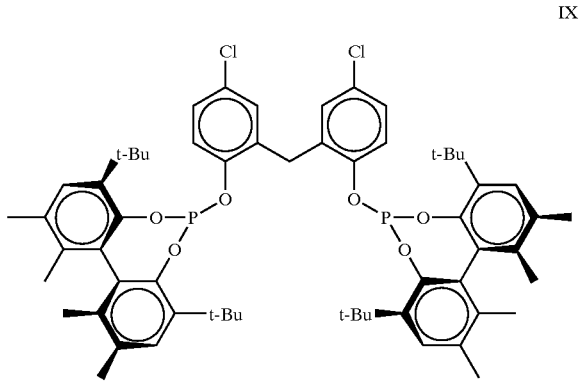

IX

Example 11

Preparation of R-BIPHEN-(2-hydroxybenzylalcohol)-bisphosphite (X)

A solution of 2-hydroxybenzylalcohol (70.7 mg, 0.570 mmol) and 240 μL Et₃N in 10 mL toluene was added to a solution of (R-BIPHEN)PBr (502 mg, 1.16 mmol) in 10 mL toluene. The solution was stirred for 14 h at ambient temperature and then filtered. The filtrate was evaporated to a white foam which was dissolved in boiling MeCN. The solution was stored at −35° C. and produced a white solid which was dried under vacuum (0.372 g, 72% yield). NMR characterization revealed the product to have the structure:

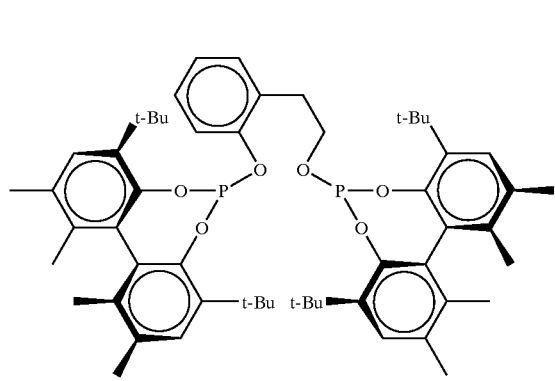

X

Example 12

Preparation of R-BIPHEN-(diphenic acid)-bisphosphite (XI)

A solution of diphenic acid (145 mg, 0.600 mmol) and 240 μL Et₃N in 10 mL toluene was added to a solution of (R-BIPHEN)PBr (522 mg, 1.20 mmol) in 10 mL toluene. The solution was stirred for 14 h at ambient temperature and then filtered. The filtrate was evaporated to a pale yellow solid which was triturated with MeCN. The resulting white solids was dried under vacuum (0.445 g, 74% yield). NMR characterization revealed the product to have the structure:

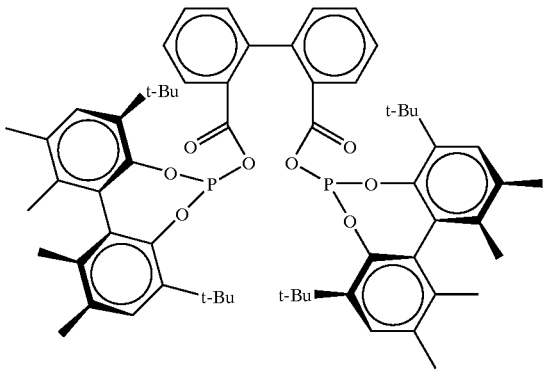

XI

Example 13

Preparation of R-BIPHEN-(succinic acid)-bisphosphite (XII)

A solution of succinic acid (74.7 mg, 0.632 mmol) and 240 μL Et₃N in 10 mL toluene was added to a solution of (R-BIPHEN)PBr (546 mg, 1.26 mmol) in 10 mL toluene. The solution was stirred for 1 h at ambient temperature and then filtered. The filtrate was evaporated to a white solid (0.551 g, 98% yield). NMR characterization revealed the product to have the structure:

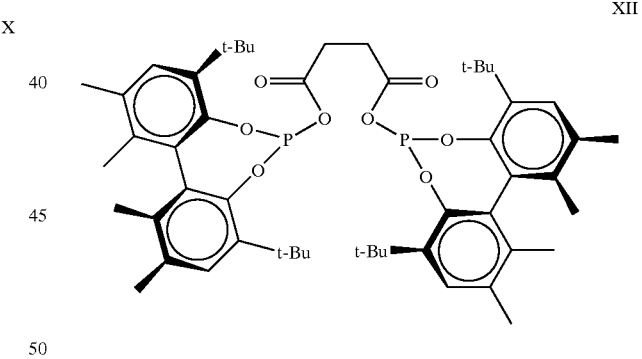

XII

Example 14

Preparation of S-(3,3'-Me₃Si-BINOL)bromidite

S-3,3'-Me₃Si-BINOL-H₂ (prepared according to the method described by van Leeuwen, et al, Organometallics, 1997, 16, 2929; 5.90 g, 14.0 mmol) was dissolved in 20 mL of toluene. Triethylamine (3.8 mL) was added. This solution was added to a solution of phosphorus tribromide (3.78 g) in 200 mL toluene. The resulting suspension was stirred for 1 h and then filtered. The filtrate was evaporated to give S-(3,3'-Me₃Si-BINOL)PBr as a pale yellow solid (7.16 g, 95% yield) having the structure:

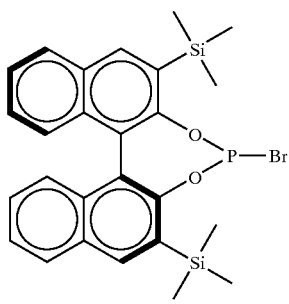

Example 15

Preparation of S-(3,3'-Me₃Si-BINOL)-neopentyl glycol-bisphosphite (XIII)

A solution of neopentyl glycol (64.2 mg, 0.616 mmol) and 260 µL Et$_3$N in 5 mL toluene was added to a solution of S-(3,3'-Me$_3$Si-BINOL)PBr (669 mg, 1.24 mmol) in 10 mL toluene. The solution was stirred for 3 h at ambient temperature and then filtered. The filtrate was evaporated to a pale yellow foamy solid which was triturated with 3 mL MeCN and then dried under vacuum (0.503 g, 80% yield). NMR characterization revealed the product to have the structure:

XIII

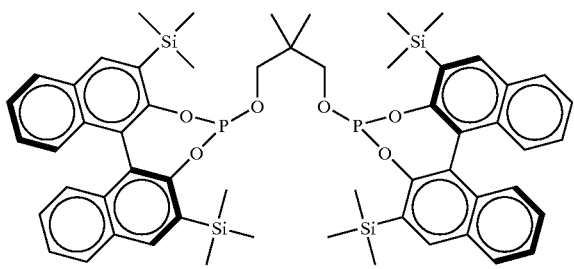

Example 16

Preparation of S-(3,3'-Me₃Si-BINOL)-biphenol-bisphosphite (XIV)

A solution of 2,2'-biphenol (107.6 mg, 0.578 mmol) and 240 µL Et$_3$N in 5 mL toluene was added to a solution of S-(3,3'-Me$_3$Si-BINOL)PBr (646 mg, 1.20 mmol) in 10 mL toluene. The solution was stirred for 3 h at ambient temperature and then filtered. The filtrate was evaporated to a pale tan solid which was triturated with 3 mL MeCN. The resulting white solid was dried under vacuum (0.59 g, 92% yield). NMR characterization revealed the product to have the structure:

XIV

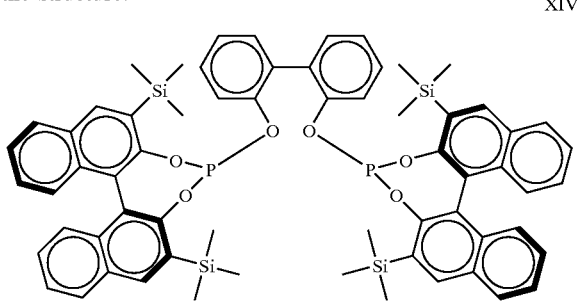

Example 17

Preparation of S-(3,3'-Me₃Si-BINOL)-ethylene glycol-bisphosphite (XV)

A solution of ethylene glycol (29.4 mg, 0.473 mmol) and 160 µL Et$_3$N in 5 mL toluene was added to a solution of S-(3,3'-Me$_3$Si-BINOL)PBr (512 mg, 0.949 mmol) in 10 mL toluene. The solution was stirred for 2 h at ambient temperature and then filtered. The filtrate was evaporated to a colorless oil (0.423 g, 91% yield). NMR characterization revealed the product to have the structure:

XV

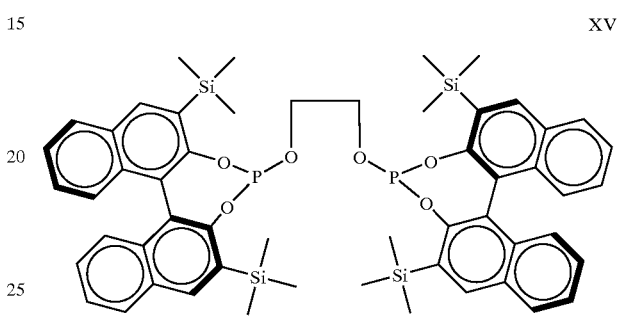

Example 18

Preparation of (R-BIPHEN)1,3-benzenedimethanol bisphosphite (XVI)

A solution of 1,3-benzenedimethanol (89.4 mg, 0.647 mmol) and 240 µL Et$_3$N in 10 mL toluene was added to a solution of (R-BIPHEN)PBr (569 mg, 1.31 mmol) in 10 mL toluene. The solution was stirred for 18 h at ambient temperature and then filtered. The filtrate was evaporated to a white solid (0.576 g, 98% yield). NMR characterization revealed the product to have the structure:

XVI

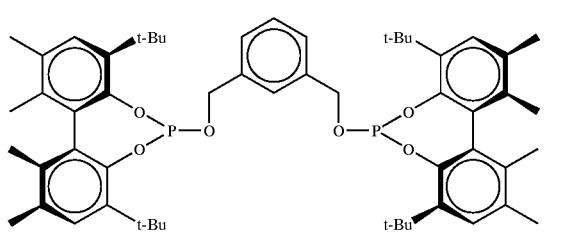

Example 19

Preparation of S-(3,3'-Me₃Si-BINOL)-1,4-butane-diol-bisphosphite (XVII)

A solution of 1,4-butanediol (33.4 mg, 0.370 mmol) and 140 µL Et$_3$N in 5 mL toluene was added to a solution of S-(3,3'-Me$_3$Si-BINOL)PBr (410 mg, 0.761 mmol) in 10 mL toluene. The solution was stirred for 3 h at ambient temperature and then filtered. The filtrate was evaporated to an oily white solid (0.359 g, 96% yield). NMR characterization revealed the product to have the structure:

XVII

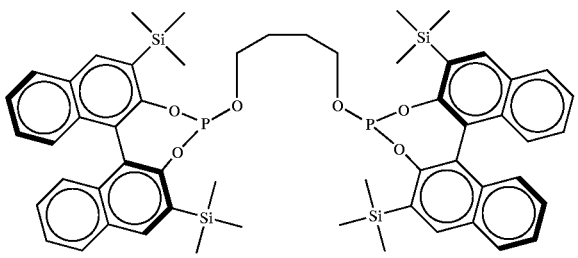

Example 20

Preparation of (R-BIPHEN) 1,4-butanediol bisphosphite (XIII)

A solution of 1,4-butanediol (55 mg, 0.61 mmol) and 200 μL Et$_3$N in 5 mL toluene was added to a solution of (R-BIPHEN)PBr (529 mg, 1.22 mmol) in 10 mL toluene. The solution was stirred for 2 h at ambient temperature and then filtered. The filtrate was evaporated to a white solid (0.506 g, 97% yield). NMR characterization revealed the product to have the structure:

XIII

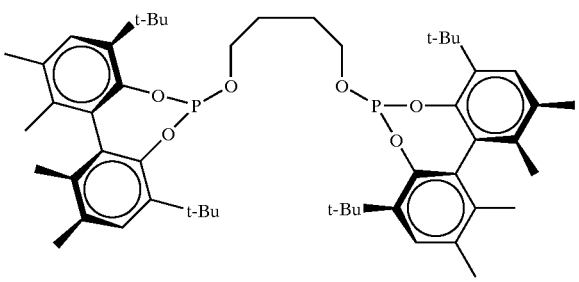

Example 21

Preparation of (R-BIPHEN)catechol bisphosphite (XIX)

A solution of catechol (169 mg, 1.53 mmol) and 460 μL Et$_3$N in 15 mL toluene was added to a solution of (R-BIPHEN)PBr (1.329 g, 3.07 mmol) in 10 mL toluene. The solution was stirred for 18 h at ambient temperature and then filtered. The filtrate was evaporated to a white solid which was triturated with acetonitrile. The resulting white solid was dried under vacuum (0.779 g, 58% yield). NMR characterization revealed the product to have the structure:

XIX

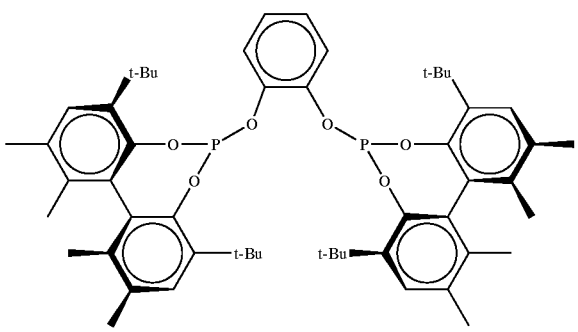

Example 22

Preparation of (R-BIPHEN) (N,N'-dimethyl-1,3-diaminopropane)bisphosphoramidite (XX)

To a 4 mL toluene solution of N,N'-dimethyl-N,N'-bis-trimethylsilanyl-propane-1,3-diamine (83.8 mg, 0.34 mmol) was added 347 mg (0.68 mmol) of (S-BIPHEN)PI (prepared by reaction of (S-BIPHEN)PBr with Me$_3$SiI in toluene). The solution was stirred for 18 h. The solution was concentrated to about 2 mL followed by addition of 4 mL of hexane. After stirring for 30 min, a white solid Was collected by filtration. The solid was dried under reduced pressure to give 246 mg (83% yield) of product. $^{31}$P{$^1$H} (C$_6$D$_6$) δ 140.9. NMR characterization revealed the product to have the structure:

XX

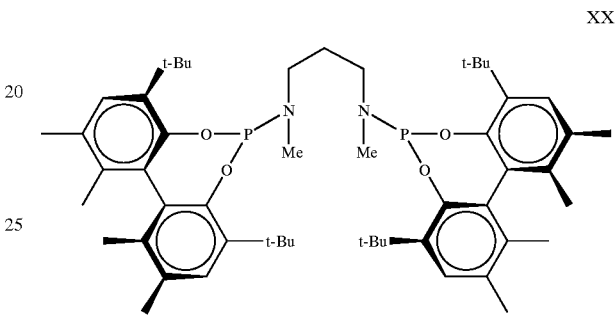

Example 23

Preparation of S-(3,3'-Me$_3$Si-BINOL)-(N,N'-dimethyl-1,3-diaminopropane)bisphosphoramidite (XXI)

S-(3,3'-Me$_3$Si-BINOL)PBr was dissolved in 4 mL of toluene. N,N'-dimethyl-N,N'-bis-trimethylsilanyl-propane-1,3-diamine was added. The reaction was stirred for 18 h then solvent was removed leaving 0.359 mg of product as off-white solid. Yield 101.6%. $^{31}$P{$^1$H} (C$_6$D$_6$) δ 149.5. NMR characterization revealed the product to have the structure:

XXI

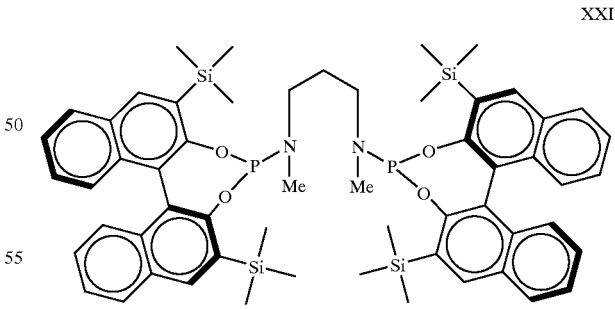

Examples (24–44)

Asymmetric Hydroformylation Using Optically Active Rh Catalysts

These examples were all performed using the same general procedure. Under a nitrogen atmosphere, Rh(CO)$_2$(acac) (5.6 mg, 0.022 mmol) and the ligand to be tested (1.1 equiv/Rh) were dissolved in acetone (5 mL). To the resulting solution was added 0.5 mL of alkene. The solutions were transferred to a reactor system that consists of eight parallel, mechanically-stirred pressure reactors. The parallel reactors each have individual temperature and pressure controls. Total volume for each reactor is 15 mL. Upon charging the catalyst solutions, the reactors were heated to the desired temperature and then pressurized with 150 psi of 1:1 $H_2/CO$. The reactions were stirred under constant pressure for 3 hours, after which the reactors were vented to atmospheric pressure. Samples were then withdrawn for analysis by chiral stationary phase gas chromatography. Vinyl acetete hydroformylation samples were analyzed using a Supelco BETA Dex-225 (30 m×0.25 mm, 250 μm film thickness) column which was capable of resolving the enantiomers of 2-acetoxypropionaldehyde and 3-acetoxypropionaldehyde for determination of enantiomeric excess (% ee) and regioselectivity (b/l). Allyl cyanide hydroformylation samples were analyzed using a Chiraldex A-TA (30 m×0.25 mm, 250 μm film thickness) column which was capable of resolving the enantiomers of 3-formylbutyronitrile and 4-formylbutyronitrile for determination of enantiomeric excess (% ee) and regioselectivity (b/l). These data are given in Tables 1 and 2.

Comparative Example 1

Asymmetric Hydroformylation Using Chiraphite-Rh Catalyst

Under a nitrogen atmosphere, $Rh(CO)_2(acac)$ (5.6 mg, 0.022 mmol) and Chiraphite (1.1equiv/Rh) were dissolved in acetone (5 mL). To the resulting solution was added 0.5 mL of alkene. The solution was transferred into one of eight parallel, mechanically-stirred pressure reactors. Upon charging the catalyst solution, the reactor was heated to the desired temperature and then pressurized with 150 psi of 1:1 $H_2/CO$. The reactions were stirred under constant pressure for 3 hours, after which the reactors were vented to atmospheric pressure. Samples were then withdrawn for analysis by chiral stationary phase gas chromatography. Vinyl acetete hydroformylation samples were analyzed using a Supelco BETA Dex-225 (30 m×0.25 mm, 250 μm film thickness) column which was capable of resolving the enantiomers of 2-acetoxypropionaldehyde and 3-acetoxypropionaldehyde for determination of enantiomeric excess (% ee) and regioselectivity (b/l). Allyl cyanide hydroformylation samples were analyzed using a Chiraldex A-TA (30 m×0.25 mm, 250 μm film thickness) column which was capable of resolving the enantiomers of 3-formylbutyronitrile and 4-formylbutyronitrile for determination of enantiomeric excess (% ee) and regioselectivity (b/l). These data are given in Tables 1 and 2.

Comparative Example 2

Asymmetric Hydroformylation Using BINAPHOS-Rh Catalyst

Under a nitrogen atmosphere, $Rh(CO)_2(acac)$ (5.6 mg, 0.022 mmol) and BINAPHOS (1.1 equiv/Rh) were dissolved in acetone (5 mL). To the resulting solution was added 0.5 mL of alkene. The solution was transferred into one of eight parallel, mechanically-stirred pressure reactors. Upon charging the catalyst solutions, the reactors were heated to the desired temperature and then pressurized with 150 psi of 1:1 $H_2/CO$. The reactions were stirred under constant pressure for 3 hours, after which the reactors were vented to atmospheric pressure. Samples were then withdrawn for analysis by chiral stationary phase gas chromatography. Vinyl acetete hydroformylation samples were analyzed using a Supelco BETA Dex-225 (30 m×0.25 mm, 250 μm film thickness) column which was capable of resolving the enantiomers of 2-acetoxypropionaldehyde and 3-acetoxypropionaldehyde for determination of enantiomeric excess (% ee) and regioselectivity (b/l). Allyl cyanide hydroformylation samples were analyzed using a Chiraldex A-TA (30 m×0.25 mm, 250 μm film thickness) column which was capable of resolving the enantiomers of 3-formylbutyronitrile and 4-formylbutyronitrile for determination of enantiomeric excess (% ee) and regioselectivity (b/l). These data are given in Tables 1 and 2.

TABLE 1

Asymmetric hydroformylation of allyl cyanide.

| Example | alkene | ligand | Temp (° C.) | % ee | b/l | % conversion |
|---|---|---|---|---|---|---|
| Comp 1 | allyl cyanide | Chiraphite | 30 | 14 | 6.1 | 14 |
| Comp 2 | allyl cyanide | Binaphos | 45 | 71 | 2.6 | 94 |
| 24 | allyl cyanide | X | 30 | 45 | 7.7 | 44 |
| 25 | allyl cyanide | I | 30 | 65 | 19 | 73 |
| 26 | allyl cyanide | II | 30 | 16 | 4.4 | 1 |
| 27 | allyl cyanide | VI | 30 | 19 | 6.1 | na |
| 28 | allyl cyanide | XI | 30 | 7 | 4.1 | na |
| 29 | allyl cyanide | XII | 30 | 20 | 3.8 | na |
| 30 | allyl cyanide | XIII | 30 | 1 | 6.6 | 96 |
| 31 | allyl cyanide | XIV | 30 | 45 | 4.4 | 71 |

TABLE 2

Asymmetric hydroformylation of vinyl acetate.

| Example | alkene | ligand | Temp (° C.) | % ee | b/l | % conversion |
|---|---|---|---|---|---|---|
| Comp 1 | VA | Chiraphite | 30 | 65 | 41 | 3 |
| Comp 2 | VA | Binaphos | 30 | 50 | 10 | 43 |
| 32 | VA | I | 30 | 90 | 208 | 10 |
| 33 | VA | IV | 30 | 32 | 232 | 74 |
| 34 | VA | IX | 30 | 49 | 21 | 33 |
| 35 | VA | X | 30 | 38 | 175 | 33 |
| 36 | VA | XI | 30 | 58 | 27 | 4 |
| 37 | VA | XII | 30 | 4 | 11 | 17 |
| 38 | VA | XIV | 30 | 67 | 90 | 7 |
| 39 | VA | XIII | 30 | 8 | 11 | 24 |
| 40 | VA | XV | 30 | 9 | 69 | 94 |
| 41 | VA | XVI | 30 | 50 | 106 | 5 |
| 42 | VA | XVII | 30 | 10 | 12 | 28 |
| 43 | VA | XVIII | 30 | 47 | 40 | 69 |
| 44 | VA | XIX | 30 | 78 | 11 | 56 |

Example 45

Hydroformylation of Neat Allyl Cyanide Using Ligand I

A 25 mL mechanically-stirred autoclave was charged with $Rh(CO)_2(acac)$ (31.6 mg, 0.122 mmol) and bisphosphite I (159 mg, 0.167 mmol). Allyl cyanide was added sparged with nitrogen to remove dissolved oxygen and then added to the autoclave. The reactor was flushed with 1:1 $H_2/CO$ and then pressurized to 108 psia. The reaction mixture was stirred under 108 psia $H_2/CO$ for 18 h at 30° C. Chiral GC analysis using a Chiraldex A-TA (30 m×25 mm, 250 μm film thickness) column indicated complete conversion with 79% ee and 19:1 b/l.

Example 46

Hydroformylation of Crotonitrile Using Ligand I

Under a nitrogen atmosphere, Rh(CO)$_2$(acac) (5.6 mg, 0.022 mmol) and bisphosphite I (29.2 mg, 0.031 mmol) were dissolved in acetone (5 mL). To the resulting solution was added 0.5 mL of crotonitrile. The solution was transferred into one of eight parallel, mechanically-stirred pressure reactors. The reactor was heated to 30° C. and then pressurized with 150 psi of 1:1 H$_2$/CO. The reaction was stirred under constant pressure for 3 hours, after which the reactor was vented to atmospheric pressure. Chiral GC analysis using a Chiraldex A-TA (30 m×0.25 mm, 250 μm film thickness) column indicated formation of 3-formylbutyronitrile in 75% ee. No linear regioisomer was detected by GC.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A hydroformylation process which comprises reacting a prochiral or chiral olefinically unsaturated organic compound with carbon monoxide and hydrogen in the presence of an optically active metal-ligand complex catalyst to produce an optically active aldehyde product, said optically active metal-ligand complex catalyst comprising a metal complexed with an optically active ligand having the formula

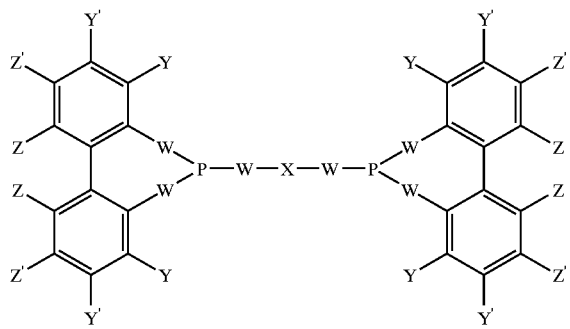

wherein each W is independently either oxygen or alkylamido (—NR), arylamido (—NAr), silylamido (—NSiR$_3$) or —NH; each Z and Y is the same or different and is a substituent other than hydrogen; each Z' and Y' is the same or different and is selected from hydrogen, substituents connected to the biaryl moieties through carbon, nitrogen, oxygen, or silicon, and halogen; Z and Z' can be optionally bridged to form a substituted or unsubstituted cyclic hydrocarbon residue; X is a substituted or unsubstituted hydrocarbon residue such that the corresponding HW—X—WH is not optically active.

2. The process of claim 1 where each Y is the same and is a substitutuent selected from tertiary alkyl, trialkylsilyl and aryl.

3. The process of claim 1 wherein each Y is tertiary alkyl.

4. The process of claim 1 where each Y is t-butyl.

5. The process of claim 1 where W—X—W is derived from 2,2'-dihydroxybiphenyl.

6. The process of claim 1 where Y is t-butyl, W—X—W is derived from 2,2'-dihydroxybiphenyl and Z and Z' are methyl.

7. The process of claim 1 in which the metal in the optically active metal-ligand complex is selected from a Group VIII, Group IB and Group VIB metal.

8. The process of claim 1 in which the metal in the optically active metal-ligand complex is a Group VIII metal.

9. The process of claim 1 in which the Group VIII metal is selected from rhodium (Rh), cobalt (Co), iridium (Ir), ruthenium (Ru), iron (Fe), nickel (Ni), palladium (Pd), platinum (Pt), osmium (Os) and mixtures thereof.

10. The process of claim 1 in which the Group VIII metal is rhodium.

11. The process of claim 1 in which the optically active metal-ligand complex catalyst is further complexed with carbon monoxide.

12. The process of claim 1 which is carried out in the added presence of free ligand.

13. The process of claim 1 in which the prochiral or chiral olefinically unsaturated organic compound comprises a substituted or unsubstituted olefin.

14. The process of claim 1 in which the olefin is of the structure

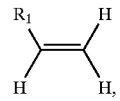

wherein
R1 and R2 are independently selected from the group consisting essentially of hydrogen; alkyl; substituted alkyl, said substitution being selected from the group consisting essentially of amino groups, alkylamino groups, dialkylamino groups, hydroxyl groups, alkoxy groups, acyloxy groups, aryl groups and substituted aryl groups wherein said aryl substitution is being selected from the group consisting essentially of alkyl groups, amino groups hydroxyl groups, alkoxy groups, acyloxy groups said aryl substitution being less than 4 substituents; alkoxy; amino; acylamino; diacylamino; nitro; carbonyl; nitrile; carboxyl; carboxamide; carboxaldehyde; carboxylic ester and alkylmercapto.

15. The process of claim 1 where the olefin is of the structure

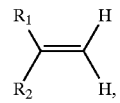

wherein
R1 and R2 are independently selected from the group consisting essentially of hydrogen; alkyl; substituted alkyl, said alkyl substitution being selected from the group consisting essentially of amino groups, alkylamino groups, dialkylamino groups, hydroxyl groups, alkoxy groups, acyloxy groups, aryl groups and substituted aryl groups wherein said aryl substitution is selected from the group consisting essentially of alkyl groups, amino groups hydroxyl groups, alkoxy groups, acyloxy groups said aryl substitution being less than 4 substituents; alkoxy; amino; acylamino; diacylamino;

nitro; carbonyl; nitrile; carboxyl; carboxamide; carboxaldehyde; carboxylic ester and alkylmercapto.

16. The process of claim 1 where the olefin is of the structure

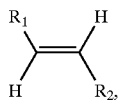

wherein
R1 and R2 are independently selected from the group consisting essentially of hydrogen; alkyl; substituted alkyl, said alkyl substitution being selected from the group consisting essentially of amino groups, alkylamino groups, dialkylamino groups, hydroxyl groups, alkoxy groups, acyloxy groups, aryl groups and substituted aryl groups wherein said aryl substitution is selected from the group consisting essentially of alkyl groups, amino groups hydroxyl groups, alkoxy groups, acyloxy groups said aryl substitution being less than 4 substituents; alkoxy; amino; acylamino; diacylamino; nitro; carbonyl; nitrile; carboxyl; carboxamide; carboxaldehyde; carboxylic ester and alkylmercapto.

17. The process of claim 1 where the olefin is of the structure

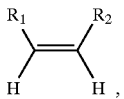

wherein
R1 and R2 are independently selected from the group consisting essentially of hydrogen; alkyl; substituted alkyl, said alkyl substitution being selected from the group consisting essentially of amino groups, alkylamino groups, dialkylamino groups, hydroxyl groups, alkoxy groups, acyloxy groups, aryl groups and substituted aryl groups wherein said aryl substitution is selected from the group consisting essentially of alkyl groups, amino groups hydroxyl groups, alkoxy groups, acyloxy groups said aryl substitution being less than 4 substituents; alkoxy; amino; acylamino; diacylamino; nitro; carbonyl; nitrile; carboxyl; carboxamide; carboxaldehyde; carboxylic ester and alkylmercapto.

18. The process of claim 1 in which the substituted or unsubstituted olefin is selected from the group consisting essentially of p-isobutylstyrene, 2-vinyl-6-methoxynaphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl)styrene, 2-ethenyl-5-benzoylthiophene, 3-ethenylphenyl phenyl ether, propenylbenzene, isobutyl-4-propenylbenzene, phenyl vinyl ether, allyl cyanide, vinyl acetate, crotonitrile, alpha-(p-trifluoromethylphenoxy)styrene or vinyl chloride.

19. The process of claim 1 where the olefin is allyl cyanide.

20. The process of claim 1 where the olefin is vinyl acetate.

21. The process of claim 1 where the olefin is crotonitrile.

22. The process of claim 1 in which the optically active product has an enantiomeric excess of greater than 50%.

23. The process of claim 1 in which the optically active product has an enantiomeric excess of greater than 75%.

24. The process of claim 1 in which the optically active product has an enantiomeric excess of greater than 90%.

25. The process of claim 1 in which the chiral olefinically unsaturated organic compound is a monosubstituted terminal olefin and the ratio of branched to linear products is greater than 4:1.

26. The process of claim 1 in which the chiral olefinically unsaturated organic compound is a monosubstituted terminal olefin and the ratio of branched to linear products is greater than 10:1.

27. The process of claim 1 in which the chiral olefinically unsaturated organic compound is a monosubstituted terminal olefin and the ratio of branched to linear products is greater than 20:1.

28. The process of claim 1 further comprising derivatizing the optically active product.

29. The process of claim 1 further comprising derivatizing the optically active product, in which the derivatizing reaction comprises an oxidation, reduction, condensation, amination, esterification, alkylation or acylation reaction.

30. An optically active ligand having the formula

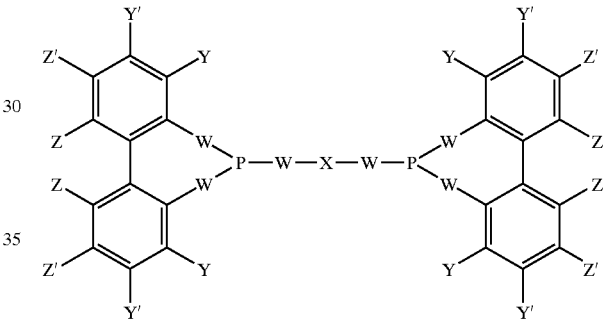

wherein each W is independently either oxygen or alkylamido (—NR), arylamido (—NM), silylamido (—NSiR$_3$) or N—H; each Z and Y is the same or different and is a substituent other than hydrogen; each Z' and Y' is the same or different and is selected from hydrogen, substituents connected to the biaryl moieties through carbon, nitrogen, oxygen, or silicon, and halogen; Z and Z' can be optionally bridged to form a substituted or unsubstituted cyclic hydrocarbon residue; X is a substituted or unsubstituted hydrocarbon residue such that the corresponding HW—X—WH is not optically active such that when Z and Z' are bridged to form a cyclic compound, then Y does not contain a silyl group.

31. A ligand of claim 30 where each W is oxygen.

32. A ligand of claim 30 where each Y is the same and is a substituent selected from tertiary alkyl, trialkylsilyl and aryl.

33. A ligand of claim 31 where each Y is tertiary alkyl.

34. A ligand of claim 30 where each Y is t-butyl.

35. A ligand of claim 30 where W—X—W is derived from 2,2'-dihydroxybiphenyl.

36. A ligand of claim 30 where Y is t-butyl, W—X—W is derived from 2,2'-dihydroxybiphenyl and Z and Z' are methyl.

37. An optically active metal-ligand complex catalyst comprising a metal complexed with an optically active ligand having the formula

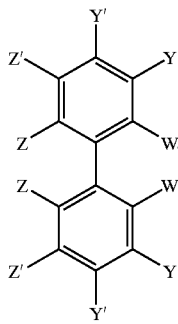 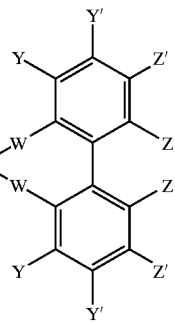

wherein each W is independently either oxygen or alkylamido (—NR), arylamido (—NAr), silylamido (—NSiR$_3$) or —NH; each Z and Y is the same or different and is a substituent other than hydrogen; each Z' and Y' is the same or different and is selected from hydrogen, substituents connected to the biaryl moieties through carbon, nitrogen, oxygen, or silicon, and halogen; Z and Z' can be optionally bridged to form a substituted or unsubstituted cyclic hydrocarbon residue; X is a substituted or unsubstituted hydrocarbon residue such that the corresponding HW—X—WH is not optically active such that when Z and Z' are bridged to form a cyclic compound, then Y does not contain a silyl group.

38. The optically active metal-ligand complex catalyst of claim 37 in which the metal is selected from a Group VIII, Group IB and Group VIB metal which comprises a metal selected from a Group VIII, Group IB and Group VIB metal.

39. The optically active metal-ligand complex catalyst of claim 37 in which the metal is a Group VIII metal.

40. The optically active metal-ligand complex catalyst of claim 37 in which metal is a the Group VIII metal selected from rhodium (Rh), cobalt (Co), iridium (Ir), ruthenium (Ru), iron (Fe), nickel (Ni), palladium (Pd), platinum (Pt), osmium (Os) and mixtures thereof.

41. The optically active metal-ligand complex catalyst of claim 37 in which the metal is rhodium.

42. The optically active metal-ligand complex catalyst of claim 37 which is further complexed with carbon monoxide.

43. An optically active metal-ligand complex catalyst precursor composition comprising
  (i) an optically active metal-ligand complex catalyst comprising a metal complexed with an optically active ligand having the formula according to claim 30;
  (ii) an organic solvent; and
  (iii) free ligand according to claim 30.

44. The process of claim 1 where each W is oxygen.

* * * * *